United States Patent [19]

Pastan et al.

[11] 4,396,628

[45] Aug. 2, 1983

[54] ANTIVIRAL ACTIVITIES OF DANSYLCADAVERINE AND CLOSELY RELATED COMPOUNDS

[75] Inventors: Ira H. Pastan, Potomac; Mark C. Willingham, Bethesda, both of Md.

[73] Assignee: The United States of America as represented by the Department of Health & Human Services, Washington, D.C.

[21] Appl. No.: 352,599

[22] Filed: Feb. 26, 1982

Related U.S. Application Data

[63] Continuation-in-part of Ser. No. 275,033, Jun. 18, 1981, abandoned.

[51] Int. Cl.$^3$ ............................................. A61K 31/18
[52] U.S. Cl. ..................................................... 424/321
[58] Field of Search ......................................... 424/321

[56] References Cited

U.S. PATENT DOCUMENTS 4,218,476  8/1980  Jöensson et al. .................... 424/321

Primary Examiner—Jerome D. Goldberg
Attorney, Agent, or Firm—John S. Roberts, Jr.

[57] ABSTRACT

The entry of animal viruses into their host cells proceeds via a specialized internalization pathway involving clathrin coated regions of the plasma membrane. In the present invention, there has been examined the effect of dansylcadaverine compared with amantadine and other antiviral agents as to the entry of vesicular stomatitis virus (VSV) into mouse cells. It was found that both compounds inhibit VSV entry. Both compounds inhibit the uptake of $\alpha_2$macroglobulin ($\alpha$2M), a protein that binds to specific membrane receptors and follows the same route of internalization. Dansylcadaverine is 20 fold more potent than amantadine to the blocking virus and also to the $\alpha_2$macroglobulin uptake.

3 Claims, 5 Drawing Figures

ANTIVIRAL ACTIVITIES OF DANSYLCADAVERINE AND CLOSELY RELATED COMPOUNDS

This application is a continuation-in-part application of abandoned Ser. No. 275,033 filed June 18, 1981.

This invention relates to the entry of animal viruses into their host cells proceeding via a specialized internalization pathway involving clathrin coated regions of the plasma membrane. In the present invention, there has been examined the effect of dansylcadaverine compared with amantadine and other antiviral agents as to the entry of vesicular stomatitis virus (VSV) into mouse cells. It was found that both compounds inhibit VSV entry. Both compounds inhibit the uptake of $\alpha_2$ macroglobulin ($\alpha 2M$), a protein that binds to specific membrane receptors and follows the same route of internalization. Dansylcadaverine is 20 fold more potent than amantadine to the blocking virus and also to the $\alpha_2$ macroglobulin uptake. The procedure or mechanics is deemed to be a cellular target for both of these amine containing compounds which is an early event in the process of receptor-mediated endocytosis, the trapping of receptor-bound ligands in clathrin-coated pit structures. The formula for dansylcadaverine and closely related amine compounds is noted below and further it is taught that about 50–500 μM is a concentration to be utilized for the inhibitor in this connection. These concentrations are utilized in an advantage of about 20 to 1 over the known amantadine antiviral compound.

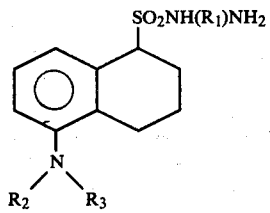

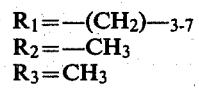

$R_1 = -(CH_2)-_{3-7}$
$R_2 = -CH_3$
$R_3 = CH_3$

PRIOR ART STATEMENT

Goodman and Gilman's, *The Pharmacological Basis of Therapeutics*, 6th edition, 1980, lists among antiviral agents in the chapter "Antiviral Agents" (pages 1240–1243) amantadine (1-adamantanamine) and ara-A, an analog of adenosine (arabinose is the 1'-epimer of ribose) tradename Vidarabine, and human interferon.

Hoffmann, "Structure, Activity and Mode of Action of Amantadine HCl and Related Compounds," *Antibiotics Chemother.*, Vol. 27, pp. 233–250 (Karger, Basel 1980).

Pastan and Willingham, "Receptor-Mediated Endocytosis of Hormones in Cultured Cells", *Ann. Rev. Physiol.*, 43:239–250, 1981.

The patent art as to dansylcadaverine may be summarized as appearing in U.S. Pat. No. 4,218,476 which lists the compound as an antithrombosis drug designed to inhibit enzymes involved in blood clotting and appears in column 1 of U.S. Pat. No. 4,218,476. There is no mention in this patent of any antiviral use.

Other patents showing related compounds are U.S. Pat. No. 2,949,479 which, however, shows the amine groups in the same ring, and U.S. Pat. No. 4,069,254 which teaches an arylsulfonamide compound.

The theory of internalization of viruses into the cell is covered and described in a separate journal article submitted to *Science*, 1981, by Ira H. Pastan and Mark C. Willingham, entitled "Journey to the Center of the Cell: Role of the Receptosome," and this article is incorporated by reference herewith.

The theory of the present invention depends on a working arrangement of how hormones bind to cells or how viral proteins bind to cells, which they do by specific receptors. The hormone or virus binds to receptors on the cell-surface and when the complexes with receptor encounter so-called coated "pits," they go into the pits until the pit is full, at which point there is a penetration or internalization. In other words, when the pit is filled with hormones or virus particles, by some mechanism which is not completely understood, the receptors then are pushed into the cells in a little vesicle which is called a receptosome. The binding of viruses is in the same manner as binding of hormones as will be demonstrated post.

TABLE 1

Effect of Dansylcadaverine, Amantadine, and Rimantadine on the Activity of Guinea Pig Liver Transglutaminase

| | Half-maximal Inhibitory Concentration |
|---|---|
| Dansylcadaverine | 0.2 mM |
| Amantadine | 20.0 mM |
| Rimantadine | 5.0 mM |

UTILITY STATEMENT

The compounds of the present invention, such as dansylcadaverine, have been tested on animals for antiviral effect and found to block a novel central regulatory pathway, thus blocking virus (such as vesicular stomatitis virus, VSV), and $\alpha_2$ macroglobulin uptake. In normal comparative procedures, the antiviral capabilities of the present dansylcadaverine are shown to be 20 times more potent than the standard reference amantadine.

A shows VSV (black arrows) and gold $\alpha_2 M$ (white arrowheads) in the same coated pit. B shows VSV (black arrows) and gold $\alpha_2 M$ (white arrowheads) with same receptosome. C shows infected Swiss 3T3 cell with VSV in coated pit. D shows a vacant coated pit of infected Swiss 3T3 in the presence of 100 μM dansylcadaverine. E shows a vacant coated pit of infected Swiss 3T3 cell in the presence of 500 μM dansylcadaverine. Membrane-bound VSV is indicated by the black arrow. F shows a vacant coated pit of infected Swiss 3T3 cell in the presence of 1 mM rimantadine. Black arrow indicates membrane-bound VSV on the same cell.

Figure 5:
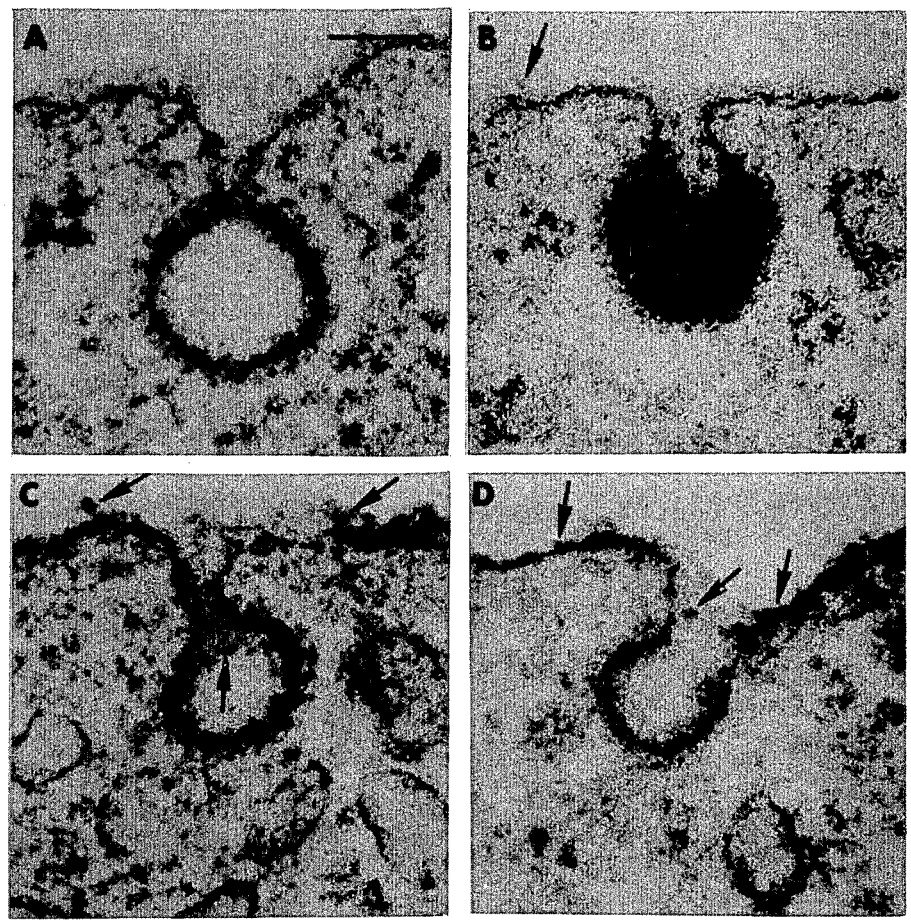

FIG. 5 shows the appearance of $\alpha_2 M$ in coated pits and its inhibitor by dansylcadaverine and amantidine. Swiss 3T3 cells were incubated with 250 μg/ml $\alpha_2 M$ at 4° C., with and without inhibitor. Em localization of $\alpha_2 M$ was performed using a peroxidase staining technique. A shows an empty coated pit of control cell. B shows $\alpha_2 M$ localized to coated pit with no inhibitor present. C shows $\alpha_2 M$ bound diffusely to the plasma membrane in the presence of 5 mM amantadine. D shows $\alpha_2 M$ bound to plasma membrane in the presence of 1 mM rimantadine; arrows illustrate bound $\alpha_2 M$.

EXAMPLE 1-A

Inhibition of Virus Internalization

Figure 1:
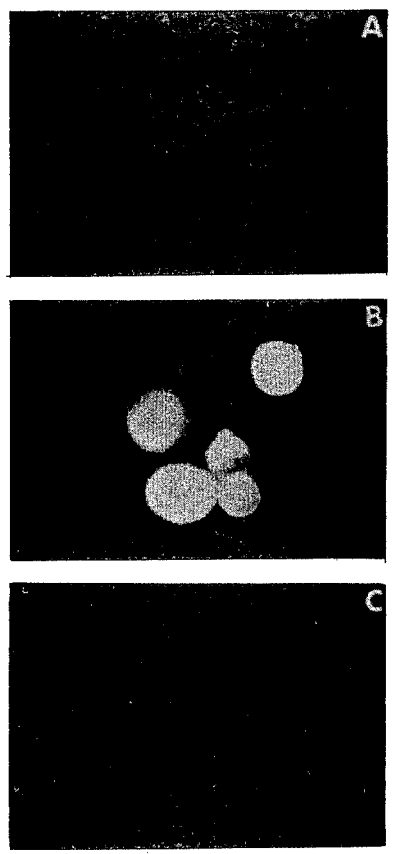
FIG. 1 shows immunofluorescent detection of VSV uptake by Swiss 3T3 cells. Swiss 3T3 cells were prebound with VSV at 4° for 60 min. (multiplicity of infection=500). The cells were then transferred to 37° C. for 10 minutes in the absence or presence of 200 μM dansylcadaverine. After removal of non-internalized VSV with trypsin-EDTA, the cells were stained for intracellular viral G-protein. A shows uninfected cells; B, VSV-infected cells; and C, VSV-infected cells—200 μM dansylcadaverine.

Virus uptake into Swiss 3T3 mouse cells was evaluated by an indirect immunofluorescence assay. Swiss 3T3 cells were exposed to VSV at a multiplicity of 500 pfu's/cell. Virus adsorption was performed at 4° C. for 60 minutes after which dansylcadaverine was added to a final concentration of 200 μM. The cultures were kept at 4° C. for an additional 5 minutes and then changed to 37° C. for 10 minutes to permit viral uptake. The cultures were trypsinized to remove externally-bound VSV virions and replated in fresh medium at 37° C. After the cells had reattached to the substratum (approximately 30–40 minutes later), they were washed with PBS, fixed with acetone, air dried, and reacted with affinity-purified rabbit anti-G protein antibody and then with rhodamine-labeled goat anti-rabbit IgG. The cells were photographed using an epifluorescence microscope. The results are shown in FIG. 1. Mock-infected cells (1A) did not stain for the virus-specific G-protein, whereas cells infected with VSV (1B) contained large amounts of intracellular G protein, indicating the internalization of VSV particles. VSV-exposed cells which had been treated with dansylcadaverine contained little or no G protein (1C) indicating dansylcadaverine had prevented VSV uptake during the 37° C. incubation period. Similar results were obtained with 5 mM amantadine (data not shown). Although the immunofluorescence results clearly indicated that dansylcadaverine and amantadine could prevent virus uptake, it was not possible to quantify the inhibitory effect with this assay. Therefore, a different technique was utilized to obtain an accurate dose-response curve.

Figure 2:
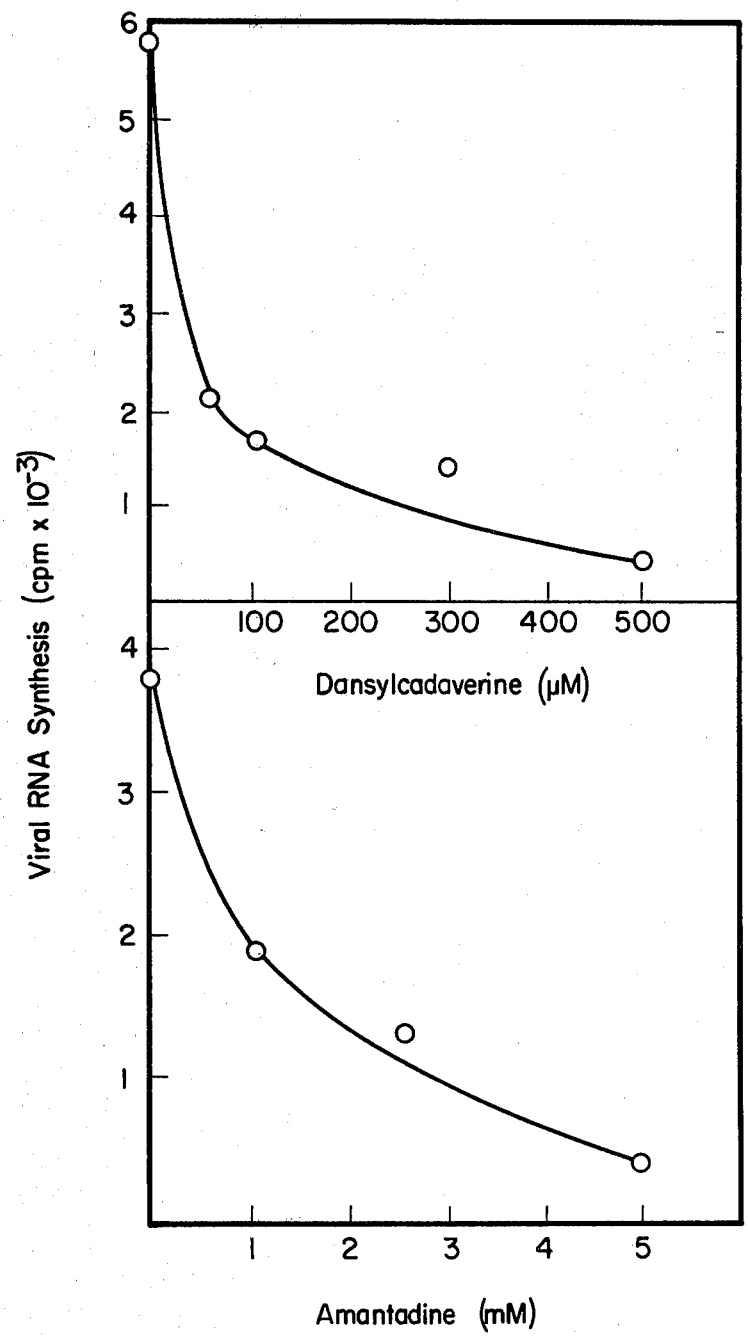
FIG. 2 shows reduction of VSV-dependent RNA synthesis by dansylcadaverine and amantadine. Confluent monolayers of Swiss 3T3 cells were infected with VSV (multiplicity of infection=500) in the presence and absence of dansylcadaverine and amantadine. Non-internalized virus was neutralized with anti-G protein antibody. Two-four hr post-infection, $H^3$-uridine incorporation into macromolecules (in the presence of actinomycin D) was used to measure VSV-dependent RNA synthesis. When VSV neutralizing antibody was omitted, control levels of VSV-dependent RNA synthesis were observed in the inhibitor-treated cultures, indicating the reversibility of dansylcadaverine and amantadine. In the absence of Actinomyosin D and VSV, cellular RNA synthesis was equivalent in control and drug-treated cultures. There was no evidence of cytotoxicity using the experimental protocol.

VSV was pre-bound to Swiss 3T3 cells by incubation at 4° C. for 60 minutes. Different concentrations of dansylcadaverine or amantadine were then added to the cell cultures which were incubated for an additional 5 minutes at 4° C. The cultures were then transferred to a 37° C. incubator for 10 minutes after which the medium was removed and fresh Dulbecco's medium (minus the inhibitors) was added and the non-internalized virus neutralized with anti-G protein antibody. Virus internalization was quantified by measuring VSV-specific RNA synthesis in the infected cells at 2.0–4.0 hr. post infection. Both dansylcadaverine and amantadine reduced VSV dependent RNA synthesis in Swiss 3T3 cells (FIG. 2). Dansylcadaverine was 20-fold more potent than amantadine. The half-maximal inhibitory concentrations of dansylcadaverine and amantadine were 50 μM and 1 mM, respectively.

EXAMPLE 1-B

Inhibition of $\alpha_2$ macroglobulin uptake

Figure 3:
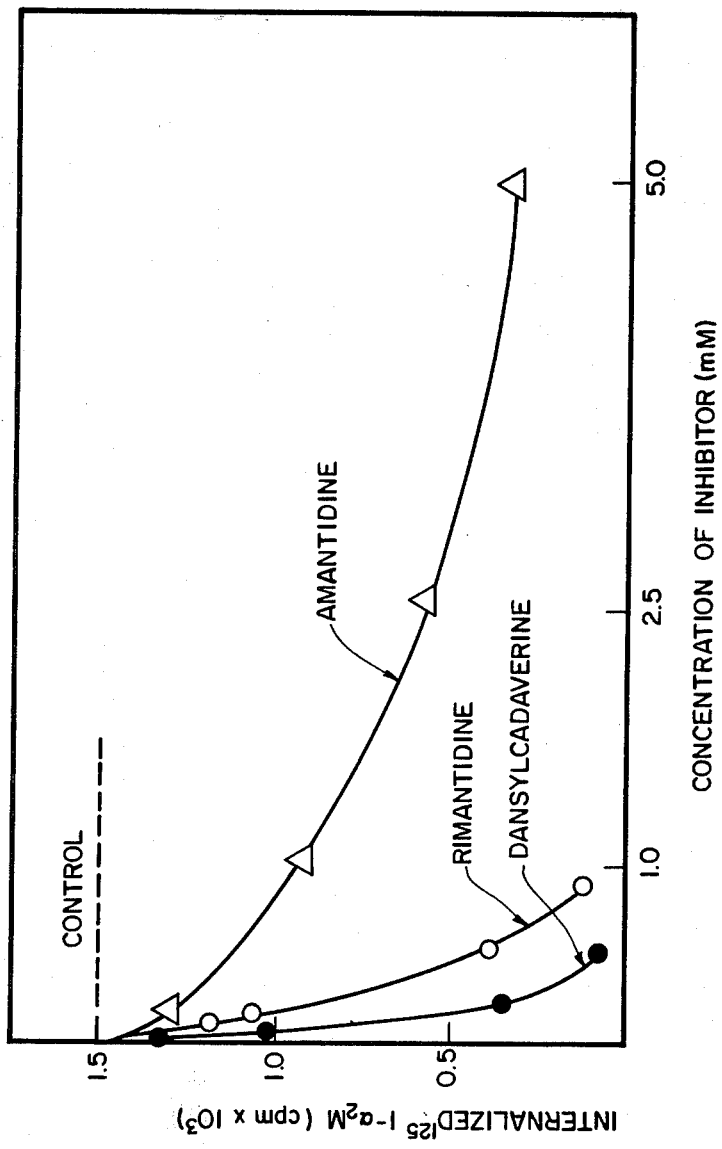
FIG. 3 shows inhibition of $I^{125}$ $\alpha_2 M$ uptake by amantadine, rimantadine, and dansylcadaverine. Confluent monolayer of Swiss 3T3 cells were exposed to 50 μg/ml $I^{125}$ $\alpha_2 M$ for 45 min. at 37° C., with and without inhibitor. Uptake of $\alpha_2 M$ was measured by methods described by Dickson, Willingham, and Pastan in *J. Biol. Chem.*, 256:3454–3459, 1981.

Dansylcadaverine, amantadine, and rimantadine (a structural analog of amantidine) were evaluated for their ability to inhibit the internalization of the protein ligand, $\alpha_2$ macroglobulin ($\alpha_2 M$). Confluent Swiss 3T3 cells were washed with serum-free medium to remove exogenous $\alpha_2 M$ and then incubated with 0.5 μg/ml $^{125}I$-$\alpha_2 M$ for 45 minutes at 37° C., with and without inhibitor. Internalization of $\alpha_2 M$ was quantified utilizing an acid protease digestion technique. FIG. 3 represents a dose-response curve for the inhibition of uptake of radiolabeled ligand by dansylcadaverine, amantidine, and rimantadine; the half-maximal inhibitory concentrations were 150 μM, 2.5 mM, and 0.5 mM, respectively. As with VSV uptake, dansylcadaverine was approximately 20-fold more potent an inhibitor than amantadine.

EXAMPLE 1-C

Block of Ligand Entry into Clathrin-Coated Pits

Figure 4:
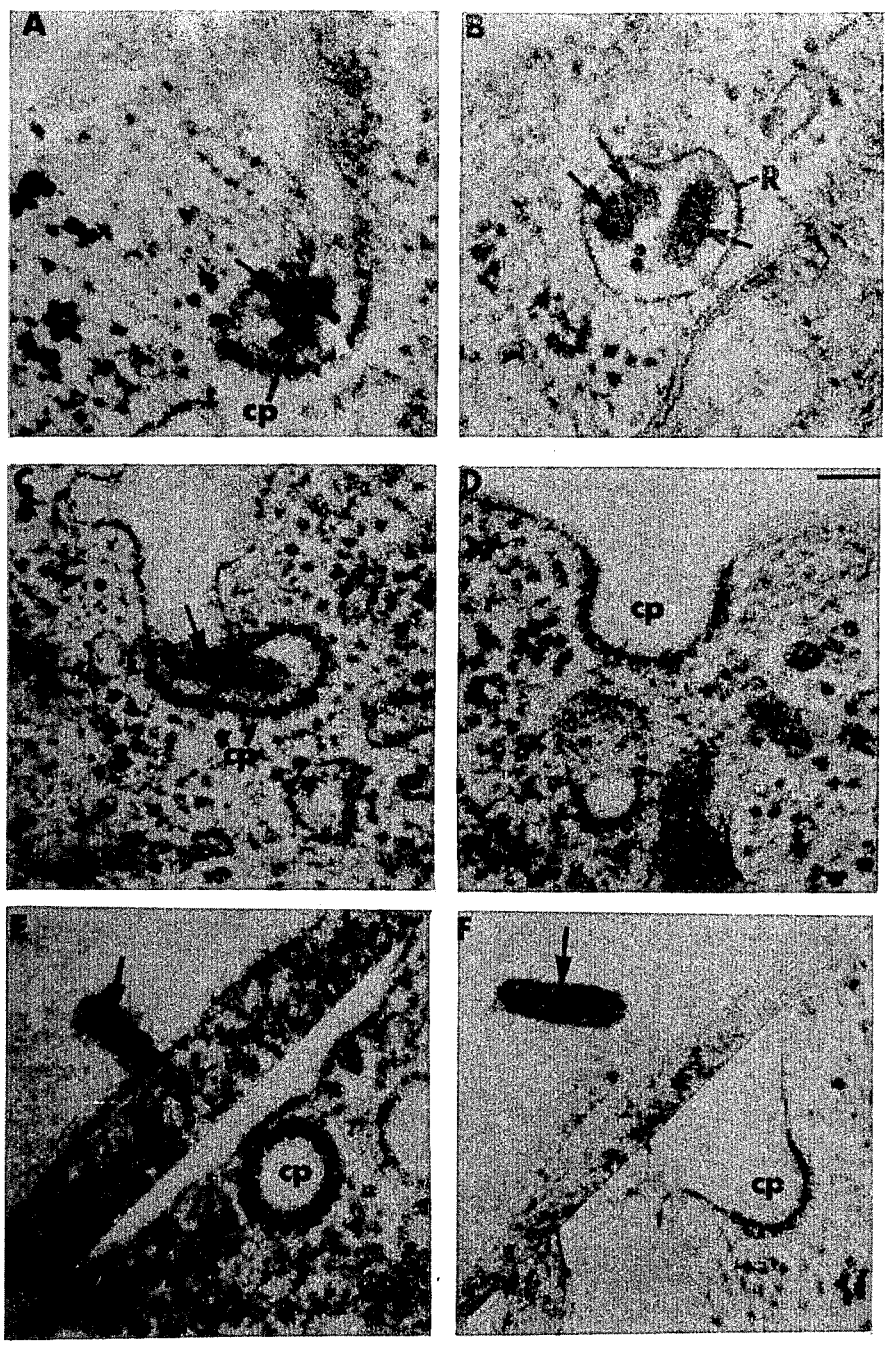
FIG. 4 indicates the co-internalization of VSV and gold-conjugated $\alpha_2 M$ and the inhibition of VSV internalization by dansylcadaverine and rimantadine. Swiss 3T3 cells were simultaneously exposed to VSV (multiplicity of infection=500) and gold-conjugated $\alpha_2 M$ (30 μg/ml). After a 2-min. incubation at 37° C., the cells were fixed and processed for EM. An analogous infection with VSV alone was performed in the presence and absence of 100 and 500 μM dansylcadaverine and 1 mM rimantadine.

Normally, both VSV and $\alpha_2 M$ are internalized via clathrin-coated pit regions of the plasma membrane. Thus, when Swiss 3T3 cells were exposed simultaneously to VSV (500 pfu's/cell) and $\alpha_2 M$ conjugated to gold (30 μg/ml), both ligands were observed within the same coated pit structures (FIG. 4A) and were internalized into the same receptosome (FIG. 4B). However, the addition of dansylcadaverine, amantidine, and rimantadine drastically perturbed this uptake mechanism. FIGS. 4C, D, E, F compare representative sections of VSV-infected cells, VSV-infected cells and 100 or 500 μM dansylcadaverine, and VSV-infected cells and 1.0 mM rimantadine. VSV virions were found in coated-pit structures of the plasma membrane in the absence of the inhibitors and only rarely in coated pits in the presence of inhibitors. In the presence of the inhibitors, almost all of the virus remained associated with non-coated plasma membrane. While in the control cells, many virus particles could be found in receptosomes 1 minute after warming to 37° C., no virus particles were seen in receptosomes in the presence of the inhibitors. This indicates that although virus may rarely enter a coated pit in the presence of these inhibitors, it does not become internalized into a receptosome.

A similar blockade was noted for the uptake of $\alpha_2 M$. Swiss 3T3 cells were incubated with $\alpha_2 M$ (250 μg/ml) for 45 minutes at 4° C. Varying concentrations of amantadine and rimantadine were present during the incubation period. The cells were then washed, fixed for EM and the $\alpha_2 M$ located by the peroxidase method. FIG. 5 illustrates the inhibition of $\alpha_2 M$ appearance in coated pits by either amantidine (FIG. 5C) or rimantidine (FIG. 5D). In the absence of inhibitors, $\alpha_2 M$ was easily detected in coated pits by the peroxidase techniques (FIG. 5B).

EXAMPLE 1-D

Inhibition of Transglutaminase Activity

The effect of dansylcadaverine, amantadine, and rimantadine on guinea pig liver transglutaminase activity is shown in Table 1, supra. Enzyme activity was measured by the incorporation of $^3$H-putrescine into casein. All three inhibitors of viral and $\alpha_2 M$ internalization were also inhibitory in the transglutaminase assay. As in their previously demonstrated ability to prevent viral uptake, the most potent compound was dansylcadaverine, the second most potent was remantadine, and the third was amantidine.

PHARMACEUTICAL CARRIERS

Pharmaceutically acceptable carriers include, but are not limited to, water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

We claim:

1. A method of inhibiting and blocking the effective entry of vesicular stomatitis virus (VSV) and $\alpha_2$ macroglobulin ($\alpha_2 M$) into mouse cells comprising administering thereto an effective blockading amount of

[Structure: bicyclic compound with SO$_2$NH(R$_1$)NH$_2$ group and N(R$_2$)(R$_3$) group]

$R_1 = -(CH_2)-_{3-7}$
$R_2 = -CH_3$
$R_3 = CH_3$ in a pharmaceutically-acceptable carrier.

2. A method according to claim 1, wherein the compound utilized $R_1 = -(CH_2)_5$, $R_2$ and $R_3 = CH_3$.

3. A method according to claim 1, wherein the concentration of the compound utilized is about 50 μM to 500 μM.

* * * * *